United States Patent [19]

Owades

[11] 4,148,873

[45] Apr. 10, 1979

[54] METHOD FOR TREATING THE SKIN WITH EXTRACTS OF HOPS

[75] Inventor: Joseph L. Owades, Boston, Mass.

[73] Assignee: S. S. Steiner, Inc., New York, N.Y.

[21] Appl. No.: 739,304

[22] Filed: Nov. 5, 1976

[51] Int. Cl.$^2$ ............................................... A61K 7/42
[52] U.S. Cl. ........................................ 424/59; 424/47; 424/168
[58] Field of Search ..................................... 424/59, 60

[56] References Cited

U.S. PATENT DOCUMENTS 2,890,225  6/1959  Gregory ............................ 424/59 X

FOREIGN PATENT DOCUMENTS 2215596  3/1972  Belgium .................................. 424/365

OTHER PUBLICATIONS

Bergwein, Amer. Perfumer & Cosmetics, 1968, vol. 83, pp. 41 to 43.
Rovesti, Chem. Abs., 1967, vol. 66, p. 22108f.
Strenkovskaya, Chem. Abs., 1973, vol. 78, p. 140384e.
Abstract of De Ment, 10/1952, vol. 663, p. 1221, D.G. 10/28/1952.
Journ. of Amer. Pharm. Assoc., 10/1958, pp. 715–717, Kokoski et al.
Umeda et al., Chem. Abs., 1955, vol. 49, p. 3466.
Chem. Abs., 1971, vol. 75, p. 143906j.
Chem. Abs., 1973, vol. 78, p. 56446c.

Primary Examiner—Dale R. Ore
Attorney, Agent, or Firm—Schiller & Pandiscio

[57] ABSTRACT

There is provided a new method of treating human skin to protect said skin from erythema-producing sunlight radiation while promoting tanning thereof, the method comprising using an active sunscreening ingredient, an ultraviolet radiation absorbing extract of hops.

6 Claims, No Drawings

METHOD FOR TREATING THE SKIN WITH EXTRACTS OF HOPS

This invention relates to novel sunscreening compositions which include an ultraviolet radiation absorbing hop extract as an active sunscreening ingredient. The present sunscreening compositions, which are non-toxic and non-irritating and can be safely applied to human skin, prevent the penetration of harmful erythematogenic radiation while transmitting non-erythematogenic ultraviolet rays which promote the tanning or bronzing of human skin.

BACKGROUND OF THE DISCLOSURE

It is generally accepted that moderate exposure to sunlight often has beneficial effects upon the human body. Apart from stimulating the circulation of blood and enhancing the formation of hemoglobin, exposure to sunlight is advocated in the treatment of tuberculosis of glands and bones and in the treatment of certain skin diseases, such as acne and psoriasis and is necessary for the in vivo formation of Vitamin D.

Overexposure to sunlight, however, may produce adverse effects, the best known of which is sunburn, with symptoms ranging from a reddening of the skin (erythema) to painful burns and blistering. More serious are effects produced in certain individuals, such as sailors and farmers, who are frequently exposed to intense sunlight. These effects include premature aging of the skin, certain types of dermatitis, and even skin cancer.

Protection of human skin against the harmful effects of sunlight can be accomplished by applying a sunscreening preparation to the skin. Many such preparations are known. In general, they contain various natural and/or synthetic compounds or materials which act as sunscreening agents by absorbing harmful erythema-producing radiation. Sunscreening agents should prevent the penetration of radiation of wavelengths between 290 mm and 315 mm, but should transmit radiation within the 315–400 mm range, which promotes tanning. Increased protection can be achieved by using compounds with a wider absorption capacity, and also by adjusting the percentage of the UV absorber used. It is also important that the sunscreening preparation be non-toxic and mild to the skin.

Substances which have been used as sunscreening agents include p-aminobenzoic acid and its derivatives, salicylates, cinnamic acid derivatives, coumarin derivatives, quinone salts, quinoline derivatives, tannic acid and its derivatives, hydroquinone and benzophenone derivatives. Still others are disclosed in Karg, U.S. Pat. Nos. 3,895,104, Strobel, 3,875,198, 3,878,229 and 3,879,443, Gerecht, 3,864,474, Norman, 3,574,825, Della Lane et al, 3,532,788, Fitzi et al, 3,624,075, Doner, 3,670,074, Welters et al, 3,781,417, Inazuka et al, 3,929,819, Richardson, 3,751,563, Catino, 3,705,234, Madigan, 3,697,642, Kläui et al, 3,920,834, the article "Sunscreens Safe and Effective Cosmetic-Drugs", by William R. Markland, COSMETICS AND TOILETRIES, March 1976, pages 79–81, and "Cosmetics" by Sagarin, Interscience Publishers, 1959, Chapter 8, pages 189–212.

Naturally occurring materials which are effective sunscreening agents include extracts of hyperium flowers, chamomile flowers, aloe leaves, helichrysum flowers, frangula bark and nut extracts, e.g., walnut husk and leaves. For more detailed information, see the article entitled "Natural Sunscreens: Vegetable Derivatives as Sunscreens and Tanning Agents", in COSMETICS AND TOILETRIES, March, 1976, pages 34–36.

It has now been surprisingly discovered that hops contain certain selective UV absorbents which act as effective sunscreening agents in the prevention of sunburn. Hops are the flower of the perennial vine, humulus lupulus. Many compounds have been identified in hops, of which the class known as the humulones are known to be most important for beer flavor. During the processing of barley malt to make beer, these humulones are isomerized to the more soluble isohumulones, which are the actual flavoring components present in all beers.

It has now been found that an extract of hops, when dissolved or dispersed in an aqueous, alcoholic or oily medium, or in a froth, and applied to the skin before exposure to the sun, effectively delays or prevents the painful effects known as erythema, or sunburn, while permitting the penetration of ultraviolet radiation which permits the formation of a sun tan. By way of illustration, the hop extract can be obtained by extracting hops with an organic solvent, such as methylene chloride or hexane, for example, recovering the hop extract from the solvent and incorporating the extract into a sunscreening composition, or the hop extract can be extracted with an alcohol or oil useful as an ingredient in sunscreening compositions and incorporated directly into the composition.

The ultraviolet absorption spectrum of many hop compounds are known and are even used in the evaluation and analysis of hops. But hop compounds have not been previously known to act as sunscreens. The effectiveness of a sunburn preventive requires not only certain ultraviolet absorbing properties, but also stability on the skin and in the presence of sunlight and perspiration, non-toxicity to animal life and the non-irritation of human skin. These additional properties have now been found to be present in hop extracts.

DESCRIPTION OF THE INVENTION

Accordingly, the present invention provides, in its broadest aspects, a sunscreening composition suitable for application to human skin, the sunscreen composition comprising as an active sunscreening ingredient, an ultraviolet radiation absorbing extract of hops.

More particularly, the sunscreening compositions of this invention comprise a physiologically acceptable cosmetic or pharmaceutical vehicle, having dispersed therein the sunscreening hops extract. This includes formulations of oil base compositions, emulsions of water-in-oil or oil-in-water, alcoholic solutions, hydro-alcoholic solutions and aerosol products. The carrier can comprise standard components such as glycerine, diethylene glycol, mineral oil, petrolatum, petroleum wax, cocoa butter, vegetable oils, lanolin, stearic acid, sesame oil, cetyl alcohol, and solvents such as ethanol, isopropanol, water, etc.

The sunscreening compositions of this invention may be in the form of lotions, creams, or ointments. In addition, these compositions may be packaged in aerosol cans and glass and plastic containers of all sizes and shapes.

The ultraviolet radiation absorbing hop extract of this invention can be obtained by contacting the flower of the humulus lupulus plant with an organic solvent, using conventional procedures of extraction. Specific conditions for carrying out the extraction will, of course, vary. By way of illustration, the hops are immersed in, or otherwise contacted with, an organic solvent at ambient temperature and atmospheric pressure or an elevated pressure of about 2 atmospheres for a period of time ranging from about ½ to about 4 hours or longer, preferably in stainless steel equipment.

A broad variety of organic solvents may be used in the extraction. By way of illustration, the solvent can be selected from among alkanes, preferably alkanes of from 5 to 12 carbon atoms, e.g., pentane, hexane, heptane, octane, nonane, decane, dodecane, and the like; alcohols, e.g., methanol, ethanol, propanol, pentanol, butanol, hexanol, octanol, nonanol, decanol, and the like; chlorinated hydrocarbons, e.g., methyl chloride, methylene chloride, and the like; petroleum ether; oils, such as mineral oil, vegetable oils, and the like, and aromatic hydrocarbons, e.g., naphtha, benzene, toluene, xylene, and the like.

After contacting the hops, the organic solvent is removed and a semi-solid residue is obtained which is a greenish, viscous liquid, almost solid at room temperatures and having a pleasant, sweet aroma. This residue, or extract, is a remarkably effective sunscreening agent. The exact chemical nature of this residue is not known, although it has been found to contain humulones and lupulones. The humulone containing hop extract may be treated to remove the major portion of the humulone fraction, e.g., by precipitation as a metallic salt, such as lead or calcium salt, and the remainder of the extract will still be effective in preventing sunburn. The humulone fraction may also be used alone as an effective sunscreening agent.

If desired, the extraction of the hops can be carried out with an alcohol or an oil which is suitable for use in the sunscreening composition. Thus, for example, the hops may be extracted with an alcohol such as ethanol, isopropanol, cetyl alcohol, or the like, or an oil such as mineral oil, sesame oil, or the like, under conditions such as described above. The alcohol or oil containing the ultraviolet absorbing hop constituents dissolved therein can then be used to prepare a sunscreening composition.

Other ingredients, such as perfumes, bodying agents, colorants, preservatives, therapeutic and antibacterial agents, surfactants, film-forming agents and the like, can be added to the sunscreening compositions in minor amounts for their conventionally employed purposes.

The relative amounts for the various ingredients in the present sunscreening compositions can vary broadly. Preferably, the ultraviolet radiation absorbing hop extract, or humulone fraction thereof, is present in amounts of at least about 2% by weight, and more preferably, from at least about 3 to at least about 10% by weight, based on the total weight of the sunscreening composition.

The compositions of this invention and methods of their preparation are further illustrated in the following examples, which are not intended to be limiting in any manner.

EXAMPLE 1

One hundred kilograms of Yakima Cluster hops are contacted with methylene chloride for ½ hour or more at room temperature and atmospheric pressure and the solvent is removed. The resulting residue, which is a greenish, viscous liquid having a sweet aroma, is dissolved in 250 l. of isopropyl alcohol and a minor amount of perfume is added. A sunscreening composition according to this invention is then obtained.

EXAMPLE 2

Using the procedure of Example 1, one-hundred kilograms of Idaho Cluster hops are extracted with hexane and the solvent is removed. The residue is treated to remove the major part of the humulones, the remainder of the hop extract is dissolved in 150 l. of isopropyl alcohol, and a minor amount of perfume is added.

EXAMPLE 3

A suntan oil according to the invention is prepared by dissolving 5 grams of hops extract, obtained using the extraction procedure of Example 1, in 50 grams of mineral oil and 45 grams of sesame oil, and adding a minor amount of perfume.

Other modifications and variations of the present invention will suggest themselves to those skilled in the art in the light of the above description. It is to be understood, therefore, that changes may be made in the particular embodiments described herein which are within the full intended scope of the invention as defined in the appended claims.

I claim:

1. A method of treating human skin to protect said skin from erythema-producing sunlight radiation while promoting tanning thereof, said method comprises applying topically to said skin in need of said treating, a sunscreening composition comprising an active sunscreening agent effective in absorbing erythema-producing ultraviolet radiation while transmitting ultraviolet radiation which promotes tanning, and a physiologically acceptable carrier for said sunscreening agent, said sunscreening agent comprising at least about 2% by weight, based on the total weight of said composition, of an organic solvent soluble extract of hops, said extract containing humulones and lupulones extracted from said hops.

2. A method as defined in claim 1 wherein said carrier comprises an aqueous medium.

3. A method as defined in claim 1 wherein said carrier comprises an alcoholic medium.

4. A method as defined in claim 1 wherein said carrier comprises an oily medium.

5. A method as defined in claim 1, wherein said carrier comprises an emulsion.

6. A method as defined in claim 1 wherein said extract of hops is present in an amount ranging from about 3 to about 10% by weight, based on the total weight of the composition.

* * * * *